United States Patent [19]

Weil et al.

[11] Patent Number: 5,712,892
[45] Date of Patent: Jan. 27, 1998

[54] APPARATUS FOR MEASURING THE BONE MINERAL CONTENT OF AN EXTREMITY

[75] Inventors: Richard Weil, Pittsford, N.Y.; David Gur, Pittsburgh, Pa.; James Frederick Owen, Rochester, N.Y.

[73] Assignee: Eastman Kodak Company, Rochester, N.Y.

[21] Appl. No.: 579,955

[22] Filed: Dec. 28, 1995

[51] Int. Cl.$^6$ .................................................. G01N 23/06
[52] U.S. Cl. ............................ 378/54; 378/56; 378/208
[58] Field of Search ........................... 378/54, 56, 89, 378/180, 207, 208

[56] References Cited

U.S. PATENT DOCUMENTS

| | | | |
|---|---|---|---|
| 3,639,764 | 2/1972 | Olson et al. | 378/180 X |
| 4,674,110 | 6/1987 | Eaton et al. | 378/208 |
| 4,941,164 | 7/1990 | Schuller et al. | 378/207 X |
| 5,122,664 | 6/1992 | Ito et al. | 378/207 X |
| 5,148,455 | 9/1992 | Stein | 378/55 |
| 5,150,394 | 9/1992 | Karellas | 378/62 |
| 5,276,328 | 1/1994 | Yoshida et al. | 250/368 |
| 5,335,260 | 8/1994 | Arnold | 378/207 |
| 5,365,564 | 11/1994 | Yashida et al. | 378/56 X |
| 5,480,439 | 1/1996 | Bisek et al. | 378/89 |

OTHER PUBLICATIONS

Cosman F, Herrington B, Himmelstein S, Lindsay R, 1991, Radiographic *Absorptiometry*: A Simple Method for Determination of Bone Mass, Osteoporosis Int. 2:34–38.

*Primary Examiner*—David P. Porta
*Attorney, Agent, or Firm*—William F. Noval

[57] ABSTRACT

Apparatus for measuring the bone density of the extremities of a human body. The apparatus includes an x-ray source for projecting a continuous spectrum x-ray beam through a body extremity region and a calibration wedge positioned adjacent to the body extremity region to produce x-ray images of the body extremity region and the calibration wedge; an x-ray image converter for converting the x-ray images into digital image signals representative of the x-ray images of the body extremity region and of the calibration wedge; and a digital image processor for processing by means of a segmentation technique the digital image signals representative of the x-ray images of the body extremity region and the calibration wedge to automatically determine the bone density of at least a portion of the body extremity region to establish whether or not there has been a loss of bone mass.

7 Claims, 3 Drawing Sheets

APPARATUS FOR MEASURING THE BONE MINERAL CONTENT OF AN EXTREMITY

FIELD OF THE INVENTION

This invention relates in general to apparatus for measuring bone density of the human body and more particularly relates to apparatus for measuring the bone mineral content of the extremities of a human body for the purpose of assessing the risk of fracture of the hip and spine due to the loss of bone mass.

BACKGROUND OF THE INVENTION

The measurement of bone density has increased significantly in recent years in large part due to the ability of bone density measurements to predict the risk of bone fractures in osteoporitic patients and due to advances in the treatment of osteoporosis.

Osteoporosis is a bone disorder characterized by the loss of bone mass, and resulting in the increased risk of bone fractures. In the United States, osteoporosis affects more than 30% of women over 45 and a smaller percentage of men. The disease is progressive with age, and affects whites and asians more than blacks. About 1.3 million fractures attributable to osteoporosis occur annually, the fractures occurring typically to the hip, spine and wrist. The cost of osteoporosis in the United States has been estimated at $3.8 billion annually. Hip fractures are particularly devastating and result in acute complications—hospitalization, depression and mechanical failure of hip replacement surgical procedures. Most patients fail to recover normal activity, and mortality within one year approaches 20%.

Osteoporosis is typically diagnosed after a fracture, although several noninvasive detection techniques involving measurement of bone density have proven promising. Generally, bone densitometry is performed in the following way. A patient is exposed to x-rays for the purpose of acquiring an x-ray image. The characteristics of the x-ray imaging device define a range of technologies including dual energy x-ray absorptiometry (DEXA), quantitative computed tomography (QCT), and film based radiographic absorptiometry. Image processing and measurement techniques specific to the acquisition technology are used to make the required bone measurements.

The typical DEXA bone densitometer system (See, e.g., U.S. Pat. No. 5,148,455, issued Sep. 15, 1992, inventor Stein, and U.S. Pat. No. 5,150,394, issued Sep. 22, 1992, inventor Karellas), consists of an x-ray source and detector which are mechanically coupled together in a C-arm fashion. The dual energy source is collimated to a specific shape (typically rectangular, fan beam, or pencil), and is imaged by a detector of the same shape. Collimation reduces the patient's exposure to x-rays for a given imaging device. Dual-energy densitometry techniques require the examination of a body part at more than one x-ray energy level. This implies that at least two x-ray images are required per patient exam. Larger area devices offer the advantage of faster imaging at the expense of reduced image quality and increased cost. Whole body and regional imaging devices are currently manufactured by companies such as Hologic, Inc. and Lunar Corp.

Both the DEXA and QCT systems are expensive, require time consuming procedure, and require considerable physical space for the equipment.

Film-based Radiographic Absorptiometry (RA) is performed today by taking an x-ray image of a body part on a piece of x-ray film. The film is then digitized and analyzed by a computer. (See, e.g., Cosman F, Herrington B, Himmelstein S, Lindsay R, 1991, *Radiographic Absorptiometry: A simple method for determination of bone mass*. Osteoporosis Int. 2:34–38.). The attenuation in the bone regions of the digital image are used to determine the bone mineral content, while the area of the bone regions are used to compute a projected volume of bone. These two measures are then used to determine the bone mass. The technique requires the use of a calibration wedge to be able to accurately calibrate out image variations from a variety of error sources including the x-ray source, positioning, film type, and film processing. Radiographic absoptiometry is typically performed on body extremities, particularly the hand. Several studies have shown that RA of the hand is effective in predicting the risk of fracture of the spine and hip as DEXA or QCT techniques performed on the spine and hip areas directly. RA offers the advantage of only requiring a single image per exam, which is captured in a single shot on a piece of x-ray film. Additionally, the x-ray source need not be configured in such a way as to be able to provide x-rays at more than a single energy, as in DEXA devices. Film-based RA is disadvantageous, however, in requiring the sending of the x-ray film to another location for digitization and analysis of the film. The inconvenience, mess and environmental problems of wet processing exposed film are also problems.

SUMMARY OF THE INVENTION

According to the present invention there is provided a solution to the problems referred to above. According to a feature of the present invention there is provided apparatus for measuring the bone density of a body extremity region, comprising;

an x-ray source for projecting a continuous spectrum x-ray beam through a body extremity region and a calibration wedge positioned adjacent to said body extremity region to produce x-ray images of said body extremity region and said calibration wedge;

an x-ray image converter for converting said x-ray images into digital image signals representative of said x-ray images of said body extremity region and of said calibration wedge; and a digital image processor for processing, by means of a segmentation technique said digital image signals representative of said x-ray images of said body extremity region and said calibration wedge to automatically determine the bone density of at least a portion of said body extremity region to establish whether or not there has been a loss of bone mass.

The present invention has the following advantages.

1. The apparatus is compact, relatively inexpensive, and fast compared to DEXA and QCT devices.

2. The apparatus provides data on loss of bone mass at the time of the x-ray procedure without the necessity of waiting for film to be digitized and analyzed as in film-based radiographic absorptiometry.

3. The mess, inconvenience, and environmental problems of film-based absorptiometry are eliminated.

4. Only a single x-ray exposure is required rather than two exposures of DEXA devices. Thus, the x-ray tube and its power supply do not need to generate two or more energy levels. Moreover, the exam may be performed in a more timely fashion.

5. Since only smaller body part extremity regions are used instead of the torso region as in DEXA and QCT devices, an area electronic sensor can be used, eliminating the necessity for structure to translate the x-ray source and detector as in DEXA systems.

DESCRIPTION OF THE EMBODIMENTS

Figure 1:
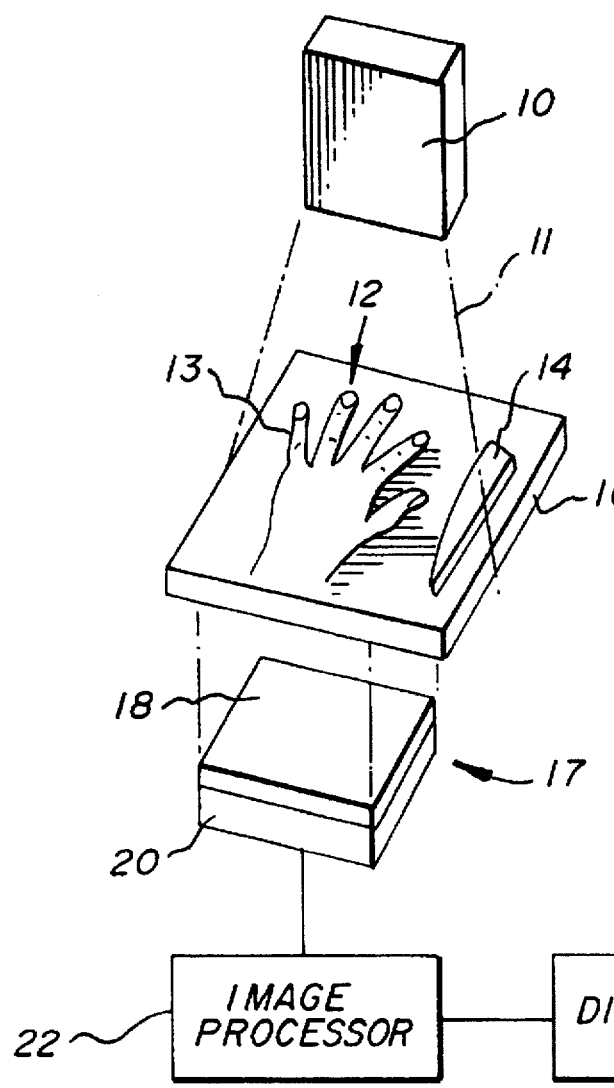
FIG. 1 is a diagrammatic perspective view of an embodiment of the present invention.

Referring now to FIG. 1, there is shown an embodiment of the present invention. As shown, an x-ray source 10 projects a continuous spectrum beam 11 of x-rays through a body extremity region (fingers of a hand) 12 and a calibration wedge 14 positioned adjacent to body extremity region 12 to produce corresponding x-ray images. Body extremity region 12 and calibration wedge 14 are supported by support 16. An x-ray converter 17 includes a scintillation screen 18 which converts the x-ray images to light images, and an area photodetector array which converts the light images to 30 digital image signals. An image processor 22 processes by means of a segmentation technique the digital image signals corresponding to the x-ray image of the body extremity region 12 and the x-ray image of the calibration wedge 14 to automatically determine the bone density of at least a portion of the body extremity region for the purpose of assessing loss of bone mass. This assessment can then be used by a diagnostician to predict the likelihood of future osteoporosis so that appropriate preventive treatment may be initiated. The images or data relating to the images can be displayed on display 24.

Any other x-ray to light converter other than a scintillation screen 18 may be used, such as an image intensifier tube. The photodetector array can be a CCD area array, an MOS area array, a photodiode array, or the like. The phantom 14 can be made of aluminum, or other materials which approximate the density variations of a human extremity. It will be understood that more than one phantom could also be used. The segmenting technique used can be any edge, region or texture based segmentation image processing technique that results in an automatic determination of the bone characteristics such as bone density.

Figure 2:
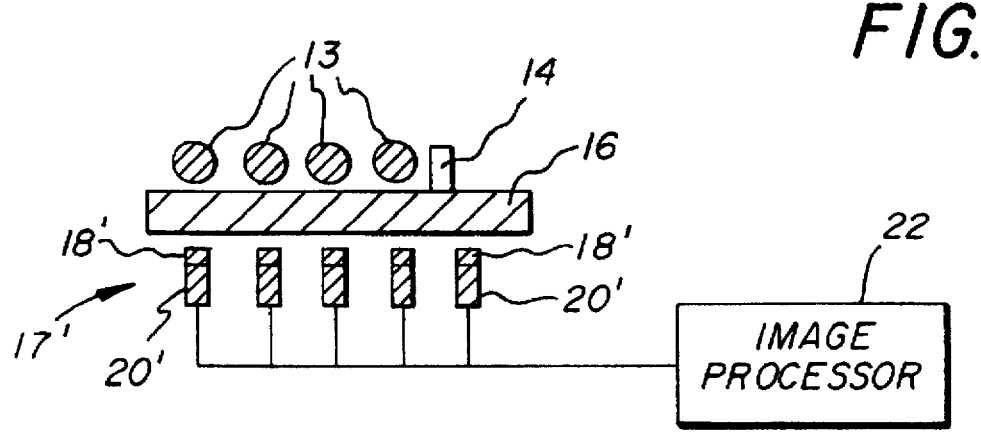
FIG. 2 is a diagrammatic view of another embodiment of the present invention.

FIG. 2 shows another embodiment of the present invention. As shown, instead of a single large x-ray converter, separate x-ray converters are located under each digit of the human extremity as well as under the phantom. Digits 13 of human extremity 12 rest on support 12, as does phantom 14. Below each digit 13 and below phantom 16 are individual x-ray converters 17' including scintillation screens 18' and photo detector arrays 20'. The outputs of converters 17' are sent to image processor 22 for processing.

Figure 3:
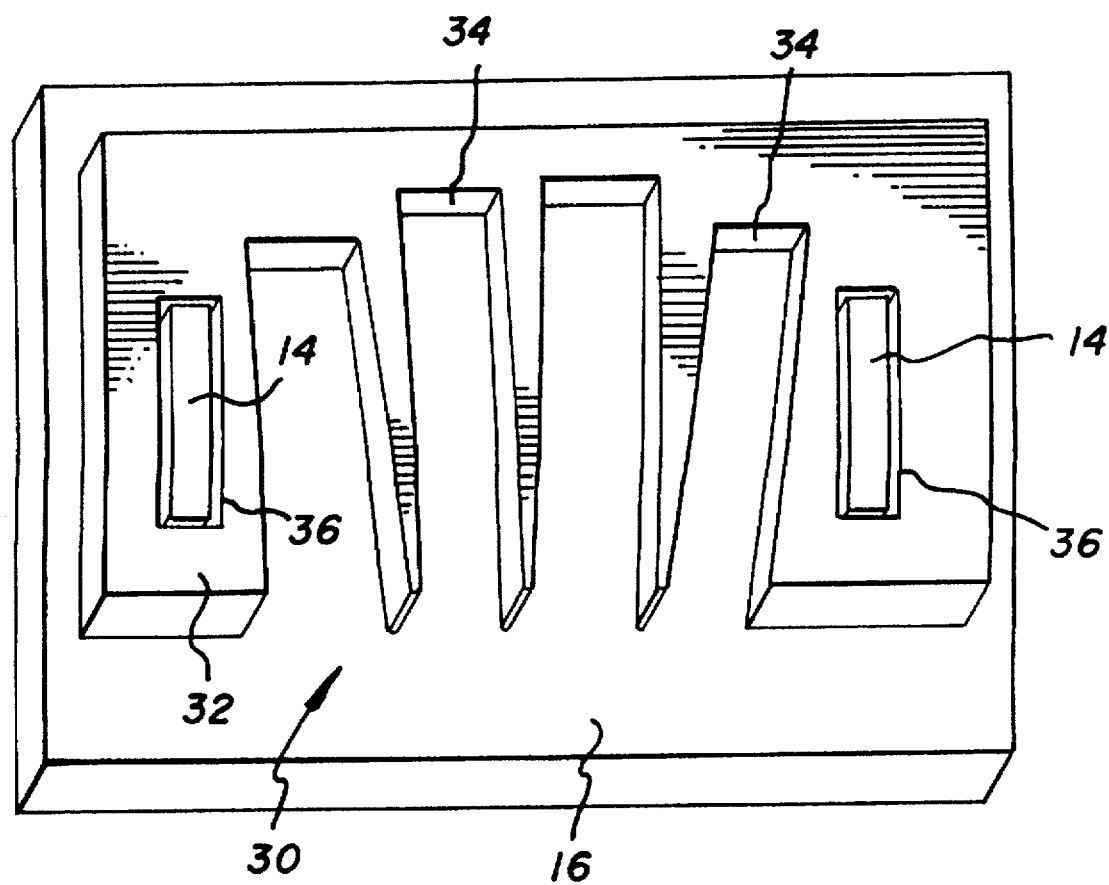
FIGS. 3 and 4 are plan views of a fixture which is useful in practicing the present invention.
Figure 4:
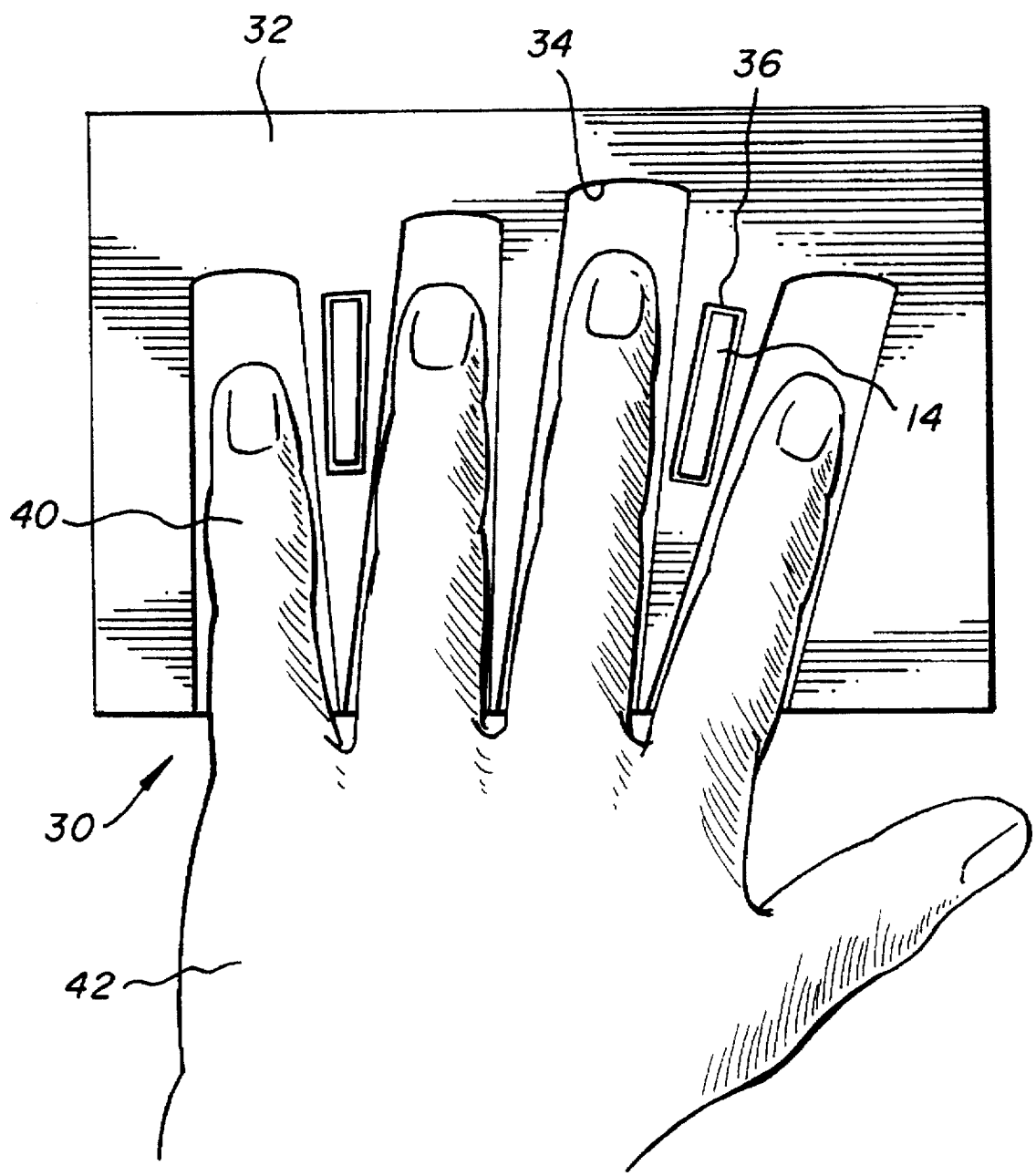

Referring now to FIGS. 3 and 4, there is shown another feature of the present invention. As shown in FIG. 3, a body extremity positioner 30 includes a body 32 having several cutouts 34 for positioning the digits 13 of a body extremity 12 (such as the fingers of a hand or the toes of a foot). Body 32 also has depressions 36 for positioning phantoms 14 adjacent to the digits 13 positioned in cutouts 34. Depressions 36 can be located outside of cutouts 34 (FIG. 3) or between cutouts 34 (FIG. 4). Cutouts 34 should be oriented so that the human digits are separated but without exerting excessive force on them that may cause discomfort (e.g., to digits which are deformed by arthritis, or the like).

FIG. 4 shows the positioning of four fingers 40 of hand 42 in the cutouts 34 of positioner 30. The positioner 30 is supported by support 16 and positions the fingers between x-ray source 10 and x-ray converter 17 within x-ray beam 11. Positioner 30 may be made of any suitable material. Preferably, positioner 30 is of a material that provides a readily identifiable spatial reference landmark in the digital images produced by converter 17. This reference landmark greatly enhances the capability of the digital imaging processing techniques used to identify individual fingers and to segment tissue from bone for bone density analysis.

The invention has been described with specific reference to certain embodiments thereof but it will be understood by those skilled in the art that modifications and alternatives are within the scope of the present invention.

What is claimed is:

1. Apparatus for determining the bone density of a human body comprising:

a body extremity positioner having several aligned cutouts for positioning the digits of a body extremity and at least one cutout aligned with said cutouts for receiving a calibration wedge which is smaller than said digits;

an x-ray source for projecting a continuous spectrum x-ray beam through body extremity digits and a calibration wedge positioned in said positioner to produce x-ray images of said digits and said calibrating wedge;

a plurality of separate x-ray image converters, positioned adjacent respective of said body extremity digits and said calibration wedge positioned in said positioner, for converting said x-ray images into digital image signals representative of said body extremity digits and of said calibration wedge; and a digital image processor for processing said digital image signals representative of said body extremity digits and said calibration wedge to determine the bone density of at least a portion of said body extremity to establish whether there has been a loss of bone mass.

2. The apparatus of claim 1 wherein said x-ray image converter includes a first converters, each, for converting said x-ray images into corresponding light images and a second converter in light communication with said first converter for converting said light images into digital image signals corresponding to said light images.

3. The apparatus of claim 2 wherein said first converter is a scintillating screen.

4. The apparatus of claim 2 wherein said first converter is an image intensifying device.

5. The apparatus of claim 2 wherein said second converter is an area photodetector array, a CCD array, an MOS array, or a photodiode array.

6. The apparatus of claim 1 wherein said positioner also positions said calibration wedge in a fixed spatial relationship relative to said digits and to said x-ray beam.

7. The apparatus of claim 1 wherein said digital image processor uses the digital image of said positioner to facilitate the processing of said digital images to determine the bone density of one or more of said digits.

* * * * *